(12) United States Patent
Nord et al.

(10) Patent No.: US 8,835,878 B2
(45) Date of Patent: Sep. 16, 2014

(54) GATED RADIATION PROCEDURE USING PACKAGES

(71) Applicant: Varian Medical Systems International AG, Zug (CH)

(72) Inventors: Janne Nord, Espoo (FI); Jarkko Peltola, Tuusula (FI)

(73) Assignee: Varian Medical Systems International AG, Cham (CH)

( * ) Notice: Subject to any disclaimer, the term of this patent is extended or adjusted under 35 U.S.C. 154(b) by 0 days.

(21) Appl. No.: 13/628,603

(22) Filed: Sep. 27, 2012

(65) Prior Publication Data

US 2013/0020510 A1     Jan. 24, 2013

Related U.S. Application Data

(63) Continuation of application No. 12/356,266, filed on Jan. 20, 2009, now Pat. No. 8,278,633.

(51) Int. Cl.
*A61N 5/00* (2006.01)
*G21G 5/00* (2006.01)
*A61N 5/10* (2006.01)

(52) U.S. Cl.
CPC ............. *A61N 5/1049* (2013.01); *A61N 5/1064* (2013.01); *A61N 5/1037* (2013.01)
USPC .................. 250/492.1; 250/453.11; 250/395; 378/65; 378/67; 378/68; 378/125; 378/150; 378/152

(58) Field of Classification Search
USPC ........ 250/492.1, 453.11, 395; 378/65, 67, 68, 378/125, 150, 152
See application file for complete search history.

(56) References Cited

U.S. PATENT DOCUMENTS

| | | | |
|---|---|---|---|
| 3,952,201 A * | 4/1976 | Hounsfield | 378/8 |
| 6,888,919 B2 | 5/2005 | Graf | |
| 7,649,981 B2 | 1/2010 | Seppi et al. | |
| 8,278,633 B2 * | 10/2012 | Nord et al. | 250/492.1 |
| 8,581,218 B2 * | 11/2013 | Fujimoto et al. | 250/492.3 |
| 2007/0003010 A1 * | 1/2007 | Guertin et al. | 378/63 |

OTHER PUBLICATIONS

Non-final Office Action dated Jun. 10, 2011, for U.S. Appl. No. 12/356,266.
Final Office Action dated Jan. 26, 2012, for U.S. Appl. No. 12/356,266.
Notice of Allowance and Fees Due dated May 15, 2012, for U.S. Appl. No. 12/356,266.

* cited by examiner

*Primary Examiner* — Jack Berman
*Assistant Examiner* — Meenakshi Sahu
(74) *Attorney, Agent, or Firm* — Vista IP Law Group, LLP

(57) ABSTRACT

A method of delivering radiation in a session includes delivering radiation towards a patient using a radiation system, wherein the radiation is delivered based at least in part on a physiological phase or a position of the patient, after the radiation is delivered, changing a configuration of the radiation system, wherein the act of changing the configuration is performed independent of at least one motion of the patient, and delivering additional radiation towards the patient after the configuration of the radiation system is changed, wherein the acts of delivering radiation and the act of changing the configuration are performed in response to a processor executing a treatment plan that prescribes a plurality of packages and a transition, the transition prescribing the act of changing the configuration of the radiation system when no radiation is being delivered by the radiation system.

28 Claims, 5 Drawing Sheets

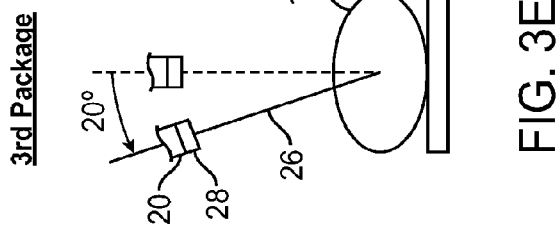
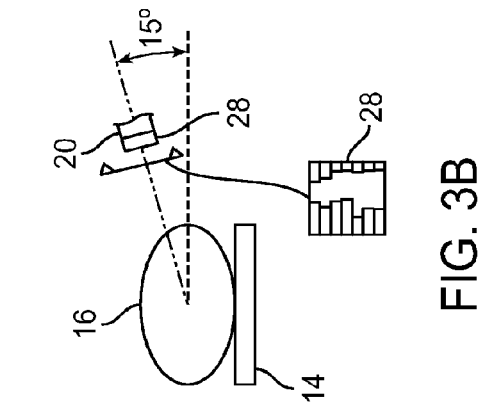 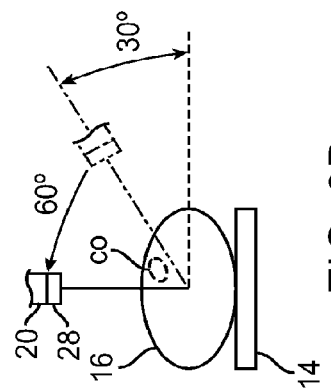
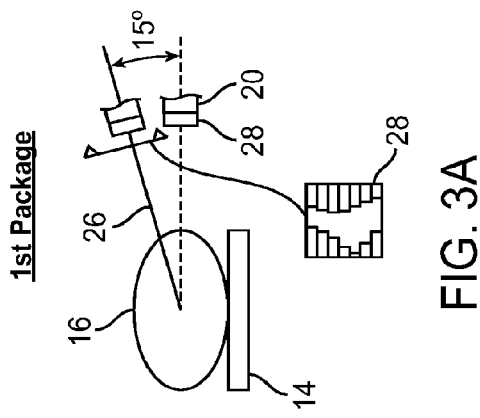 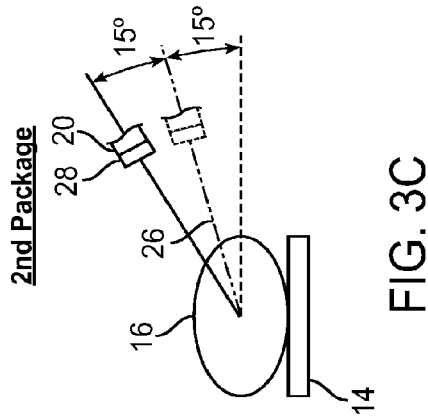

GATED RADIATION PROCEDURE USING PACKAGES

RELATED APPLICATION DATA

This application is a continuation of U.S. patent application Ser. No. 12/356,266, filed on Jan. 20, 2009, pending, the entire disclosure of which is expressly incorporated by reference herein.

FIELD

This application relates generally to gated radiation procedure, and more specifically, to systems and methods for performing gated radiation procedure, such as a treatment procedure or an imaging procedure.

BACKGROUND

Radiation has been employed to image and treat tumorous tissue. In radiation therapy, a high energy beam is applied from an external source towards the patient. The external source, which may be rotating (as in the case for arc therapy), produces a collimated beam of radiation that is directed into the patient to the target site. The dose and placement of the dose must be accurately controlled to ensure that the tumor receives sufficient radiation, and that damage to the surrounding healthy tissue is minimized.

Sometimes, in a radiation treatment procedure, a plurality of treatment sessions may be performed. In each treatment session, a radiation source may be placed at a prescribed gantry angle to thereby deliver radiation beam towards a target tissue from a certain angle. As a result of delivering radiation towards the target tissue from a plurality of different angles, a sufficient radiation dose may be delivered to the target tissue to thereby treat the target tissue, while surrounding healthy tissue may be protected.

Patient movement during radiation delivery may significantly affect the outcome of the procedure. For example, in a radiation treatment procedure, patient movement affects dose distribution in patient. One method of controlling this phenomenon is to use gated treatment. In gated treatment, dose is only delivered while patient is in a position or phase (e.g., breathing phase) that is prescribed for radiation delivery. For example, in a treatment plan, the radiation may be prescribed to be delivered only when the patient is relatively stationary (e.g., when the patient is in full inhale or exhale positions) for some period of time, and when there are not any unnecessary critical organs that would receive radiation when a target in the patient is radiated.

In existing gated treatment methods, the treatment has been planned as one continuous delivery. The operation of the radiation machine is stopped to pause the continuous delivery when the patient is not in a planned phase or position. The operation of the radiation machine is resumed only when the patient is back in a planned phase or position. Therefore the time when patient is not in planned phase or position is lost in delivery efficiency sense.

SUMMARY

In accordance with some embodiments, a method of delivering radiation in a session includes delivering radiation towards a patient using a radiation system, wherein the radiation is delivered based at least in part on a physiological phase or a position of the patient, after the radiation is delivered, changing a configuration of the radiation system, wherein the act of changing the configuration is performed independent of at least one motion of the patient, and delivering additional radiation towards the patient after the configuration of the radiation system is changed, wherein the acts of delivering radiation and the act of changing the configuration are performed in response to a processor executing a treatment plan that prescribes a plurality of packages and a transition, the transition prescribing the act of changing the configuration of the radiation system when no radiation is being delivered by the radiation system.

In accordance with other embodiments, a system for delivering radiation in a session includes a processor, wherein the processor is configured for generating a first signal to cause a radiation system to deliver radiation towards a patient based at least in part on a physiological phase or a position of the patient, generating a second signal for changing a configuration of the radiation system after the radiation is delivered, wherein the processor is configured to change the configuration of the radiation system independent of at least one motion of the patient, and generating a third signal to cause the radiation system to deliver additional radiation towards the patient after the configuration of the radiation system is changed, wherein the processor is configured for generating the first, second, and third signals in accordance with a treatment plan that prescribes a plurality of packages and a transition, the transition prescribing the act of changing the configuration of the radiation system when no radiation is being delivered by the radiation system.

In accordance with other embodiments, a computer product includes a medium for storing a set of instruction, an execution of which causes a process for delivering radiation in a session to be performed, the process comprising delivering radiation towards a patient using a radiation system, wherein the radiation is delivered based at least in part on a physiological phase or a position of the patient, after the radiation is delivered, changing a configuration of the radiation system, wherein the act of changing the configuration is performed independent of at least one motion of the patient, and delivering additional radiation towards the patient after the configuration of the radiation system is changed, wherein the acts of delivering radiation and the act of changing the configuration are performed in response to the processor executing a treatment plan that prescribes a plurality of packages and a transition, the transition prescribing the act of changing the configuration of the radiation system when no radiation is being delivered by the radiation system.

In accordance with other embodiments, a system for use to deliver radiation in a session includes a medium having all or a portion of a treatment plan, or information derived therefrom, wherein the treatment plan prescribes a plurality of packages and a transition, wherein one of the plurality of packages prescribes a delivery of radiation when a patient is in a prescribed physiological phase or position, and the transition prescribes a changing of a configuration of a radiation system when no radiation is being delivered by the radiation system, and a processor for generating one or more signals to operate the radiation system based at least in part on the all or the portion of the treatment plan, or the information derived from the treatment plan.

In accordance with other embodiments, a method of determining a treatment plan includes determining a plurality of packages and a transition, wherein one of the plurality of packages prescribes a delivery of radiation when a patient is in a prescribed physiological phase or position, and the transition prescribes a changing of a configuration of a radiation system when no radiation is being delivered by the radiation system, and storing or receiving information regarding the plurality of packages and the transition.

In accordance with other embodiments, a system for determining a treatment plan includes a processor for determining a plurality of packages and a transition, wherein one of the plurality of packages prescribes a delivery of radiation when a patient is in a prescribed physiological phase or position, and the transition prescribes a changing of a configuration of a radiation system when no radiation is being delivered by the radiation system, and a medium for storing information regarding the plurality of packages and the transition.

Other and further aspects and features will be evident from reading the following detailed description of the embodiments, which are intended to illustrate, not limit, the invention.

BRIEF DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments and are not therefore to be considered limiting of its scope.

FIGS. 3A-3E illustrate an example of radiation delivery that is performed based on packages of a treatment plan in accordance with some embodiments;

DESCRIPTION OF THE EMBODIMENTS

Figure 1:
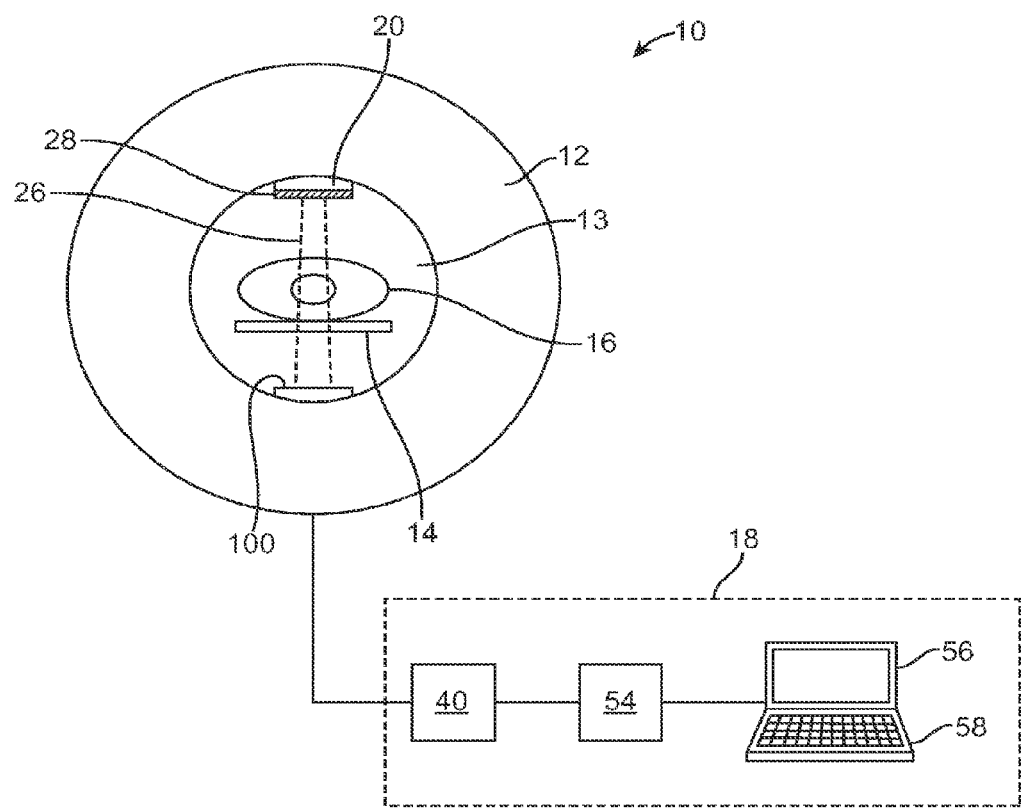
FIG. 1 illustrates a radiation system in accordance with some embodiments.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

FIG. 1 illustrates a radiation treatment system 10 for delivering radiation in accordance with a treatment plan that is determined using techniques described herein. As used in this specification, the term "treatment plan" is not limited to a complete plan for treatment, and may refer to a part of a plan for treatment, such as one or more parameters that are for use to carry out a treatment, or information derived therefrom (e.g., information derived from a plan for treatment, such as information derived from one or more parameters). The system 10 includes a gantry 12, a patient support 14 for supporting a patient 16, and a control system 18 for controlling an operation of the gantry 12. The system 10 also includes a radiation source 20 that projects a beam 26 of radiation towards a patient 16 while the patient 16 is supported on support 14, and a collimator system 28 for controlling a delivery of the radiation beam 26. For example, in some embodiments, the collimator system 28 may include a plurality of leaves for changing a shape of the beam 26. In other embodiments, the collimator system 28 may be rotatable (e.g., relative to an axis of the beam 26). The radiation source 20 can be configured to generate a cone beam, a fan beam, or other types of radiation beams in different embodiments.

In the illustrated embodiments, the radiation source 20 is a treatment radiation source for providing treatment energy. In other embodiments, in addition to being a treatment radiation source, the radiation source 20 can also be a diagnostic radiation source for providing diagnostic energy. In such cases, the system 10 will include an imager, such as the imager 100, located at an operative position relative to the source 20 (e.g., under the support 14). In some embodiments, the treatment energy is generally those energies of 160 kilo-electron-volts (keV) or greater, and more typically 1 mega-electron-volts (MeV) or greater, and diagnostic energy is generally those energies below the high energy range, and more typically below 160 keV. In other embodiments, the treatment energy and the diagnostic energy can have other energy levels, and refer to energies that are used for treatment and diagnostic purposes, respectively. In some embodiments, the radiation source 20 is able to generate X-ray radiation at a plurality of photon energy levels within a range anywhere between approximately 10 keV and approximately 20 MeV. Radiation sources capable of generating X-ray radiation at different energy levels are described in U.S. patent application Ser. No. 10/033,327, entitled "RADIOTHERAPY APPARATUS EQUIPPED WITH AN ARTICULABLE GANTRY FOR POSITIONING AN IMAGING UNIT," filed on Nov. 2, 2001, and U.S. patent application Ser. No. 10/687,573, entitled "MULTI-ENERGY X-RAY SOURCE," filed on Oct. 15, 2003. In further embodiments, the radiation source 20 can be a diagnostic radiation source. In the illustrated embodiments, the radiation source 20 is coupled to the gantry 12. Alternatively, the radiation source 20 may be located within a bore.

In the illustrated embodiments, the control system 18 includes a processor 54, such as a computer processor, coupled to a control 40. The control system 18 may also include a monitor 56 for displaying data and an input device 58, such as a keyboard or a mouse, for inputting data. In the illustrated embodiments, the gantry 12 is rotatable about the patient 16, and during a treatment procedure, the gantry 12 rotates about the patient 16 (as in an arch-therapy). In other embodiments, the gantry 12 does not rotate about the patient 16 during a treatment procedure. In such case, the gantry 12 may be fixed, and the patient support 14 is rotatable. The operation of the radiation source 20, the collimator system 28, and the gantry 12 (if the gantry 12 is rotatable), are controlled by the control 40, which provides power and timing signals to the radiation source 20 and the collimator system 28, and controls a rotational speed and position of the gantry 12, based on signals received from the processor 54. Although the control 40 is shown as a separate component from the gantry 12 and the processor 54, in alternative embodiments, the control 40 can be a part of the gantry 12 or the processor 54.

It should be noted that the system 10 is not limited to the configuration described above, and that the system 10 may have other configurations in other embodiments. For example, in other embodiments, the system 10 may have a different shape. In other embodiments, the radiation source 20 of the system 10 may have different ranges of motions and/or degrees of freedom. For example, in other embodiments, the radiation source 20 may be rotatable about the patient 16 completely through a 360° range, or partially through a range that is less than 360°. Also, in other embodiments, the radiation source 20 is translatable relative to the patient 16. In further embodiments, the source 20 may be coupled to the gantry 12 via an arm, in which case, the source 20 is located outside the bore of the gantry 12.

Although the above embodiments have been described with reference to delivering treatment radiation that is in the form of x-rays, in other embodiments, the system and technique described herein may be used for other types of treatment energy. For examples, in other embodiments, the radiation source 20 may be a proton source (in which case, the radiation system is a proton system) for delivering protons to treat a patient, an electron source for delivering electrons, or other types of particle source for delivering other types of particles for treating patient. Accordingly, embodiments of the system and method described herein may be used in other types of treatment, such as proton treatment, which may be considered to be a type of radiation treatment. Also, it should be noted that the term "collimator" is not limited to a device having leafs for blocking radiation, and may refer to a device having one or more jaws or jaw blocks. Thus, a position of a collimator may refer to position of leafs of a collimator, position of collimator jaws, or a global position of the collimator itself relative to some coordinate system (e.g., a position of the collimator relative to a gantry or relative to a radiation machine, etc.).

Figure 2:
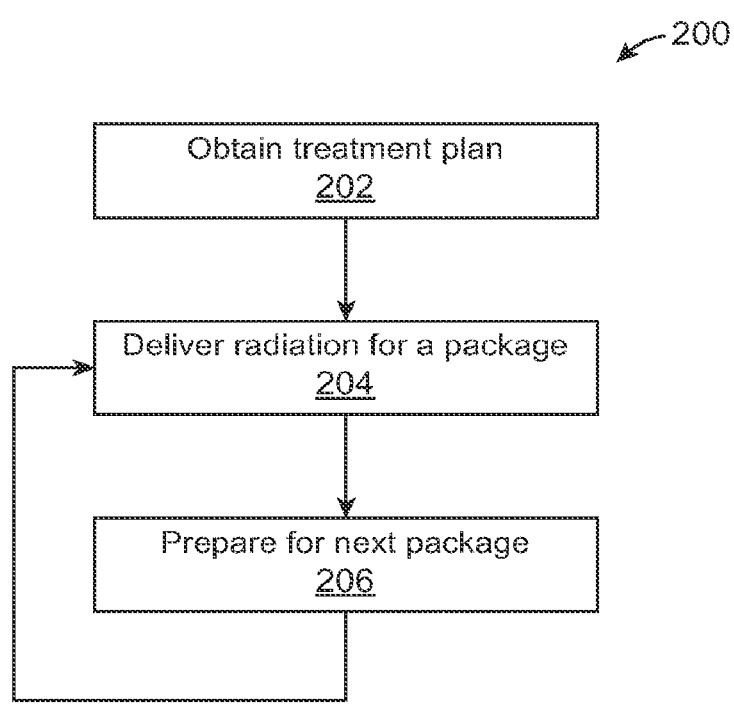
FIG. 2 illustrates a method of performing a radiation procedure in accordance with some embodiments.

FIG. 2 illustrates a method 200 of delivering radiation in accordance with some embodiments. In the illustrated embodiments, the method 200 is performed during a session to treat the patient 16. As used in this specification, the term "session" refers to a procedure that is performed within a certain period, such as, within a day, several hours, several minutes, or other duration of time. In some embodiments, the patient 16 remains in a treatment room and/or remains supported on the patient support 14 during the session.

First, a radiation treatment plan for a treatment is obtained (step 202). This may be performed by the processor 54 receiving the treatment plan, e.g., in a form of an electronic file. The received treatment plan may include a complete plan for treatment, a part of the plan for treatment (such as one or more parameters), or information derived from the plan. In other embodiments, the act of obtaining the treatment plan may be performed by the processor 54 retrieving the treatment plan from a medium, such as a memory. In the illustrated embodiments, the treatment is planned as a series of delivery packages and transitions between packages. Thus, the treatment plan includes a plurality of radiation delivery packages.

Next, the radiation system 10 is used to deliver radiation based on a delivery package of the treatment plan (step 204). In the illustrated embodiments, in response to the processor 54 processing the treatment plan, the radiation system 10 is operated to deliver radiation towards a target region in the patient 16. Such may be accomplished by the processor 54 generating one or more control signals to operate the radiation source 20, the collimator 28, the gantry 12, the patient support 14, or any combination of the foregoing. The delivery package is delivered while the patient 16 is in a planned phase or position. For example, in some embodiments, the patient 16 may be instructed to breath-hold to maintain at a breathing phase. While the patient 16 is at the breathing phase or position, the radiation system 10 delivers radiation according to the package of the treatment plan. The radiation system 10 may rotate the radiation source 20, move the collimator leaves, move the patient support 14, or any combination of the foregoing. In some embodiments, the moving of the collimator leaves is performed to adjust a shape of the beam 26 such that the beam 26 corresponds (e.g., conforms) to a shape of the target region. In other embodiments, the moving of the collimator leaves is performed to adjust a shape of the beam 26 such that a portion of a target region receives relatively more radiation than another portion of the target region, as in an intensity-modulated radiation therapy (IMRT).

In other embodiments, a breathing monitoring system may be employed to determine a breathing phase or position of the patient 16. In such cases, the patient 16 is allowed to breathe (inhale and/or exhale) while the radiation system 10 delivers radiation according to the package of the treatment plan. The processor 54 is configured to receive information regarding a breathing phase or position of the patient 16, and operate the radiation system 10 to deliver radiation towards the patient 16 in synchronization with the breathing of the patient 16. For example, the processor 54 may generate one or more signals to move the radiation source 20, move the collimator leaves, move the patient support 14, or any combination of the foregoing, in synchronization with the breathing of the patient 16. The breathing monitoring system and the processor 54 track the breathing behavior of the patient 16 as radiation is being delivered. In some embodiments, the breathing monitoring system may include one or more cameras aimed at the patient 16. The camera(s) detect one or more markers (which may be an object or a landmark on the patient 16) on the patient and the processor 54 processes the images from the camera(s) to determine a position or a breathing phase of the patient 16. In some embodiments, the breathing phase may have a value that ranges from 0° to 360°, and may represent a degree of completeness of a breathing cycle in which 0° corresponds to a beginning of a cycle, and 360° corresponds to an end of a cycle. Other breathing monitoring systems may also be used in other embodiments.

After the first package has been delivered, the radiation system 10 stops the delivery of radiation, and prepares for the next package in accordance with the treatment plan (step 206). For example, the processor 54 may generate one or more signals to operate components of the radiation system 10, such as, to move the radiation source 20, to move collimator leafs, to move the patient support 14, or any combination of the foregoing. In some embodiments, the operation of the radiation system 10 to prepare for the next delivery package may be performed to address various constraints imposed on the treatment. For example the radiation source 20 may move around a region where radiation is not allowed to be delivered. In another example, the patient support 14 may be moved to another position using faster speed because there are no movement correlation constraints. In the illustrated embodiments, the transition from one delivery package to the next deliver package is performed even when the patient 16 is not in a planned phase or position. This has the benefit of improving efficiency because the time when the patient 16 is not in a planned phase or position is not lost, but is instead use to prepare the radiation system 10 for a next radiation delivery. The above feature is especially beneficial in arc treatments because arc treatments are restricted by continuity of leaf movements. For example, using the above technique, the collimator leaf openings may move across a spine (e.g., to a desirable configuration for next radiation delivery) during a transition between radiation deliveries when there is no dose delivered, thereby utilizing the time that would have been lost due to the patient 16 being in an incorrect breathing phase or position.

In some embodiments, while the radiation system 10 is being operated in the transition phase to prepare for the next radiation delivery package, the radiation system 10 is not completely deactivated. For example, the radiation source 20 may be operated to stop the delivery of radiation, but other components of the radiation system 10 may remain activated so that the radiation system 10 is in a state in which it is ready for delivering additional radiation for the next delivery package. This is advantageous in that it allows radiation to be delivered quickly as soon as the radiation system 10 is ready for the next delivery package, without having to go through significant idling time that may result from the startup and initialization of the radiation system 10 if the radiation system 10 is completely deactivated.

In some embodiments, while the configuration of the system 10 is being changed, the radiation system 10 is in a state in which the radiation system 10 is capable of automatically delivering additional radiation upon a detection of one or more desired conditions. For example, in some embodiments, a desired condition for delivering additional radiation may be an end of a transition phase, in which case, when the act of changing the configuration of the radiation system 10 is completed, the system 10 automatically delivers additional radiation towards the patient. In another example, the position or the physiological phase of the patient may be monitored (e.g., using a monitoring device) while the configuration of the system 10 is being changed in the transition phase. In such cases, the system 10 automatically delivers additional radiation when the act of changing the configuration of the system 10 has been completed, and when the patient is at a desired physiological phase (e.g., breathing phase) or a desired position (e.g., breathing position). In some embodiments, the processor 54 may be configured to receive information regarding a position or a physiological phase of the patient from a monitoring device. During use, when the processor 54 detects that the configuration of the system 10 has been changed (e.g., end of the transition phase), and when the processor 54 determines that the desired patient position or physiological phase has been reached, the processor 54 then generates a signal to cause the system 10 to deliver additional radiation. In some embodiments, the system 10 includes a button (e.g., a safety button), wherein when the button is un-pressed, the system 10 is prevented from delivering radiation. In such cases, the system 10 may be configured to automatically deliver additional radiation by having a user press the button during at least a part of the transition phase, such that when the desired condition(s), such as, end of transition phase, achievement of a desired position or physiological phase by the patient, etc., for delivering additional radiation is detected (e.g., by the processor 54), the system 10 can automatically deliver the additional radiation without having to wait for additional input from the user. In other cases, the system 10 may not include a safety button, and the system 10 may be configured to automatically deliver additional radiation by configuring the processor 54 to generate a signal to cause the system 10 to deliver additional radiation when the desired condition(s) is detected. In some embodiments, the system 10 may be in the state for automatically delivering radiation for an entire period in which the configuration of the system 10 is being changed. In other embodiments, the system 10 may be in the state for automatically delivering radiation for a part of an entire period in which the configuration of the system 10 is being changed.

In some embodiments, the sequence of the delivery packages in the treatment plan may be predetermined. In such cases, during the transition phase between delivery packages, the radiation system 10 is operated so that its configuration at the end of the transition conforms with the requirement of the next delivery package in the fixed sequence. In other embodiments, the sequence of the delivery packages in the treatment plan is not predetermined, but is determined in real time. In such cases, after the radiation system 10 is operated in the transition phase (e.g., to address certain constraint(s) in the treatment, such as to avoid a critical organ), the processor 54 determines the next delivery package to be delivered based on the configuration of the radiation system 10 resulted from the transition phase. For example, at the end of the transition phase, the radiation source 20 may be at gantry angle=60°, and the processor 54 may select a delivery package (from a plurality of delivery packages in the treatment plan), such as one that requires the radiation source 20 to be at or near gantry angle=60°, to perform the next radiation delivery.

Returning to FIG. 2, after the radiation system 10 has prepared for the next package, then the radiation system 10 is used to deliver radiation in accordance with the next package of the treatment plan. As shown in the figure, the delivery of radiation for a package (step 204) and the preparation of the radiation system 10 for a next package (step 206) are repeated until all of the packages of the treatment plan have been delivered.

In some embodiments, if the patient 16 becomes out of phase (e.g., the actual breathing phase does not match a prescribed phase, or does not lie within a prescribed phase range, for radiation delivery), or out of position, before a delivery of a package is completed, the radiation machine then stops the delivery of beam, and waits for the right phase to occur in order to complete the package before moving on to a transition or to a next package. In such cases, the breathing monitoring system continues to determine the patient's position and transmit signals to the processor 54 for analysis even when the patient 16 has become out of phase. The processor 54 continues to receive and analyze the signals, and when the processor 54 determines that the proper phase has occurred, it then transmits control signals to operate the system 10 to continue with the delivery of the package until it is finished.

In other embodiments, instead of waiting for the patient 16 to achieve the correct phase to complete the delivery of the current package, when the system 10 detects that the patient 16 is out of phase or position during a delivery of a package, the processor 54 may transmit control signals to operate the system 10 to deliver another package. In such cases, when the processor 54 detects that the patient's 16 breathing is not in a planned phase or position, the processor 54 then generates a signal to cause the radiation source 20 to stop beam delivery for the current package. In some cases, the processor 54 may place the current package in a hold state for a prescribed duration to see if the patient 16 can re-achieve a prescribed phase (for delivery of the remaining portion of the current package). Implementing the hold state for a prescribed duration allows the system 10 to wait for the patient 16 to re-achieve a proper phase when the patient 16 becomes out of phase that may be due to coughing, for example. If the patient 16 does not re-achieve the prescribed phase within the prescribed duration, the processor 54 then determines another package for delivery. In such cases, the processor 54 marks the current package that has been only partially delivered, and determines in real time the next package for delivery. In some embodiments, based on the current configuration of the radiation system 10 (e.g., position of the radiation source 20, collimator 28, leaves' positions, patient support 14 position, etc.) when the system 10 stops delivering radiation for the current package, and based on the requirements of the remaining packages that need to be delivered, the processor 54 may select one of the packages for execution. For example, the processor 54 may select one of the packages having delivery requirements (e.g., prescribed source position, prescribed leaves' positions, etc.) that are the closest to those of the current system configuration (e.g., current source position, current leaves' positions, etc.). In such cases, the processor 54 then generates control signals to operate the system to deliver the selected package. In the illustrated embodiments, the processor 54 is configured to operate the system 10 until all of the packages have been delivered. Thus, if there is any package (e.g., package that has been marked) that is only partially delivered, the processor 54 may go back and operate the system 10 to complete the package delivery.

As shown in the above embodiments, the radiation treatment is planned as a series of delivery packages and transitions between packages. The delivery packages are delivered while the patient 16 is in prescribe phase(s) or position(s). After a package of the treatment plan has been delivered, the radiation machine 10 may prepare for the next package, such as, by moving gantry and/or collimator leafs (e.g., to next optimal configuration). This transition may be performed even when the patient 16 is not in a correct phase or position for radiation delivery.

FIGS. 3A-3E illustrate an example of a gated radiation delivery that is package-based. The example will be described with reference to treating a patient with lung cancer using arc treatment in a treatment session. However, it should be understood that the package-based technique may be applied to treat other body parts, and/or in other types of treatment other than arc treatment. In the illustrated example, the arc treatment is delivered in three delivery packages. In the first package, the gantry 12 rotates starting from the right of the patient 16 (FIG. 3A). During the first package, the gantry 12 rotates 15 degrees while the collimator is operated (e.g., one or more of its leaves are moved) to modulate dose rate. In some cases, this is performed during a first breath hold. In other embodiments, this is performed in correspondence with the patient's 16 breathing (e.g., breathing position or breathing phase). In such cases, instead of or in addition to modulating dose rate, the collimator may be operated during the first package to track a target region.

Between first and second packages, the collimator leaves move to new configuration, and no radiation is delivered by the radiation source 20 (beam is off) (FIG. 3B). Also, the gantry 12 does not rotate between first and second packages—i.e., the radiation source 20 stays at the 15° position. At the end of the transition, the radiation system 10 remains in a stand-by mode so that it is ready to deliver additional radiation.

In the second delivery package, the radiation source 20 move another 15 degrees (in gantry angle) to deliver radiation (FIG. 3C). During the second delivery package, the collimator may be operated to modulate dose rate and/or to track a target region.

Between the second and third delivery packages, the radiation source 20 does not delivery radiation (beam is off), and the gantry 12 rotates 60 degrees and passes gantry angles where user has requested no dose (FIG. 3D). For example, at the gantry angles where no dose is desired, the patient CT data may be missing from that region, or there may be an especially critical organ (CO) in that region. At the end of the transition, the radiation system 10 remains in a stand-by mode so that it is ready to deliver additional radiation.

The third delivery package begins when the patient's 16 breath hold state is reached, and/or when the patient's 16 breathing has been successfully tracked. During the third delivery package, the gantry rotates 20 degrees while the collimator 28 moves its leaves (and/or rotate) to modulate dose rate and/or to track the target region (FIG. 3E).

As illustrated in the above embodiments, the beam off time (which was previously considered useless) is used in gated treatments to transition the radiation system 10 to more favorable configuration. By operating the radiation system 10 (i.e., not allowing the radiation system 10 to be static) during the beam off state, the time that the beam is off is not completely lost, and is utilized favorably during the treatment. Also, allowing a machine operation to be out of synchronization with patient movements during at least a part of a treatment is advantageous over methods where the whole treatment is synchronized to patient movements. This is because it does not matter how machine configurations change with respect to the patient movement during beam off time, and thus, the inventors determine that it is desirable not to maintain synchronization between the machine operation and patient movements during beam off time. Maintaining the synchronization even during beam off time and/or while the patient is not in good configuration (e.g., a desired breathing phase or position) for radiation delivery would unnecessarily constraint the operation of the radiation system 10, and would unnecessarily require larger tolerances and margins in the operation of the radiation system 10.

In any of the embodiments described herein, the operation of the radiation system 10 may include other action(s). For example, in other embodiments, the operation of the radiation system 10 (during a delivery package or during a transition between delivery packages) may include rotation of the collimator 28 (e.g., about an axis that is parallel to the beam 26). This may be performed instead of, or in addition to, moving the collimator leaves. Also, in other embodiments, the operation of the radiation system 10 may include tilting of the gantry 12 (if the gantry 12 is tiltable) about one or more axes, and/or tilting of the radiation source 20 about one or more axes (e.g., about an axis that forms an angle with the gantry 12's axis).

Figure 4:
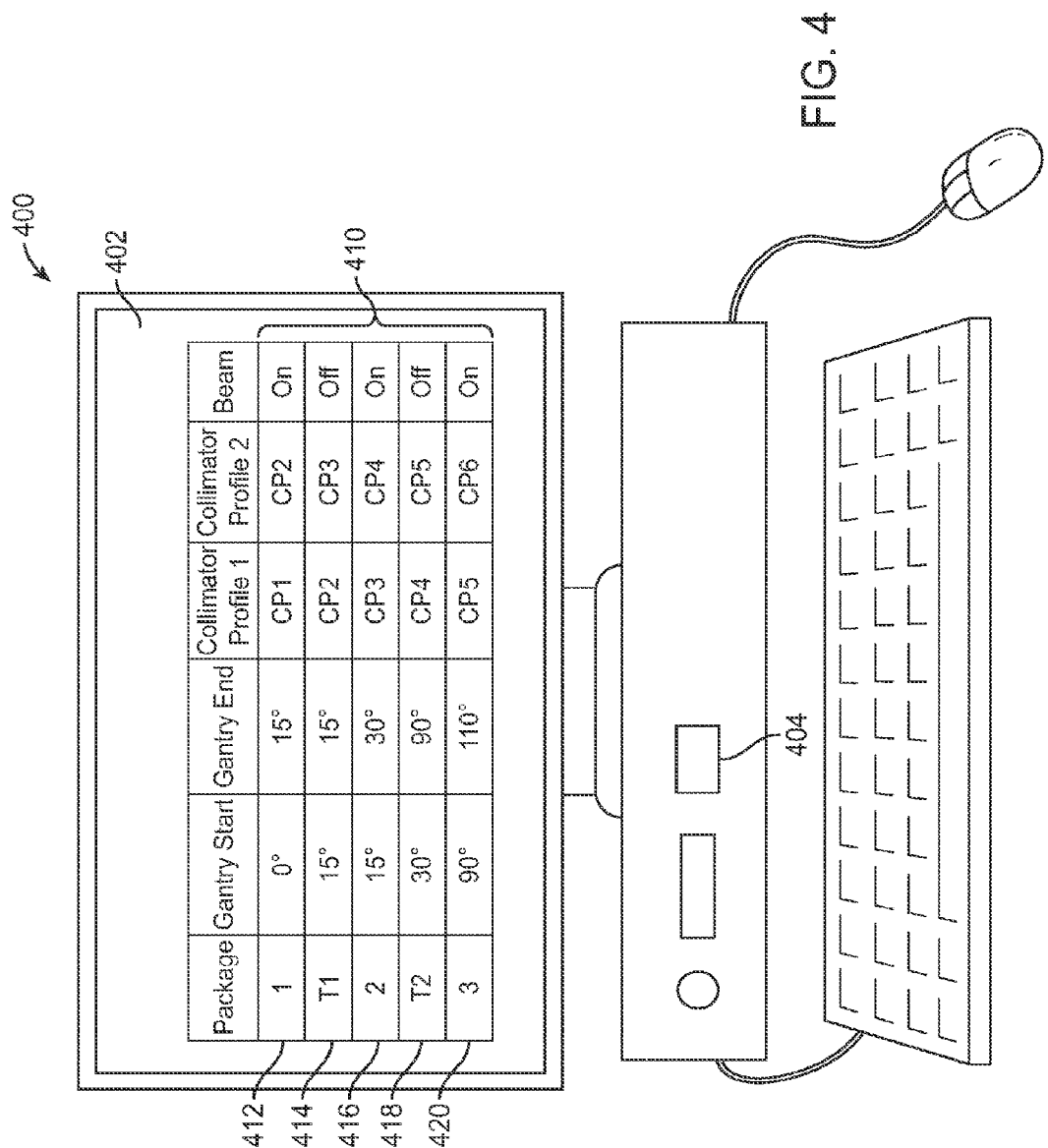
FIG. 4 illustrates a user interface for allowing a user to determine a treatment plan with a plurality of packages.

FIG. 4 illustrates a user interface 400 that may be used to determine a package-based radiation delivery plan in accordance with some embodiments. The user interface 400 includes a screen 402 displaying graphics for allowing a user to input information. The graphics may be generated by a processor 404 in response to the processor 404 executing a set of instruction. In some embodiments, the processor 404 may be implemented using the processor 54 of FIG. 1. In the illustrated embodiments, the user interface 400 presents a plurality of input fields 410 for allowing parameters for different packages and transitions to be determined and/or input. As shown in the figure, the user interface 400 includes rows 412, 416, 418 that correspond with the first, second, and third delivery packages, respectively, described in the example of FIG. 3. In particular, each of rows 412, 416, 418 includes input fields for prescribing a starting gantry angle, an ending gantry angle, a collimator configuration at the start of the gantry angle, a collimator configuration at the end of the gantry angle, and a beam on/off status. The user interface 400 also includes a row 414 of input fields that corresponds with the first transition between the first and second delivery packages, and a row 418 of input fields that corresponds with the second transition between the second and third delivery packages. Each of the rows 414, 418 includes input fields for prescribing a starting gantry angle, an ending gantry angle, a collimator configuration at the start of the gantry angle, a collimator configuration at the end of the gantry angle, and a beam on/off status.

It should be noted that the parameters that may be displayed by the interface 400 and/or input using the interface 400 are not limited to those described, and that other parameters can be used as well. Examples of parameters include a target fluence, a dose, a dose rate, a gantry position, a gantry speed, a leaf sequence, a collimator position, a beam energy, a beam-on condition, a beam-off condition, tilt angle of a gantry, tilt angle of a radiation source, and a patient support position. In some embodiments, the parameters may be determined (e.g., calculated) automatically by a processor using an optimization algorithm. In other embodiments, the parameters may be determined by a user inputting them via the user interface 400. In further embodiments, some of the parameters may be determined by a processor, while other parameters may be determined by the user.

After the parameters have been determined, the parameters may be saved in a medium as a treatment plan, or a part of a treatment plan. In some embodiments, the treatment plan, or a part of the treatment (such as one or more parameters) may be sent to the processor (such as processor 54) of the radiation machine so that the processor can use the parameter(s) to carry out the treatment plan. In other embodiments, information may be derived from the treatment plan, and the processor is configured to use the information to carry out the treatment plan.

Although the above embodiments have been described with reference to treating a patient, in other embodiments, the techniques described herein may be used in a diagnostic procedure, such as an imaging procedure. For example, in some embodiments, an imaging plan may include a plurality of radiation delivery packages, wherein one or more of the packages prescribe how imaging radiation is to be delivered. For example, a package of the imaging plan may prescribe that radiation is to be delivered at a certain gantry angle or gantry angle range. Thus, as used in this specification, the term "radiation" may refer to treatment radiation or imaging radiation. Similarly, as used in this specification, the term "treatment plan" may refer to a therapy plan or an imaging plan.

Computer System Architecture

Figure 5:
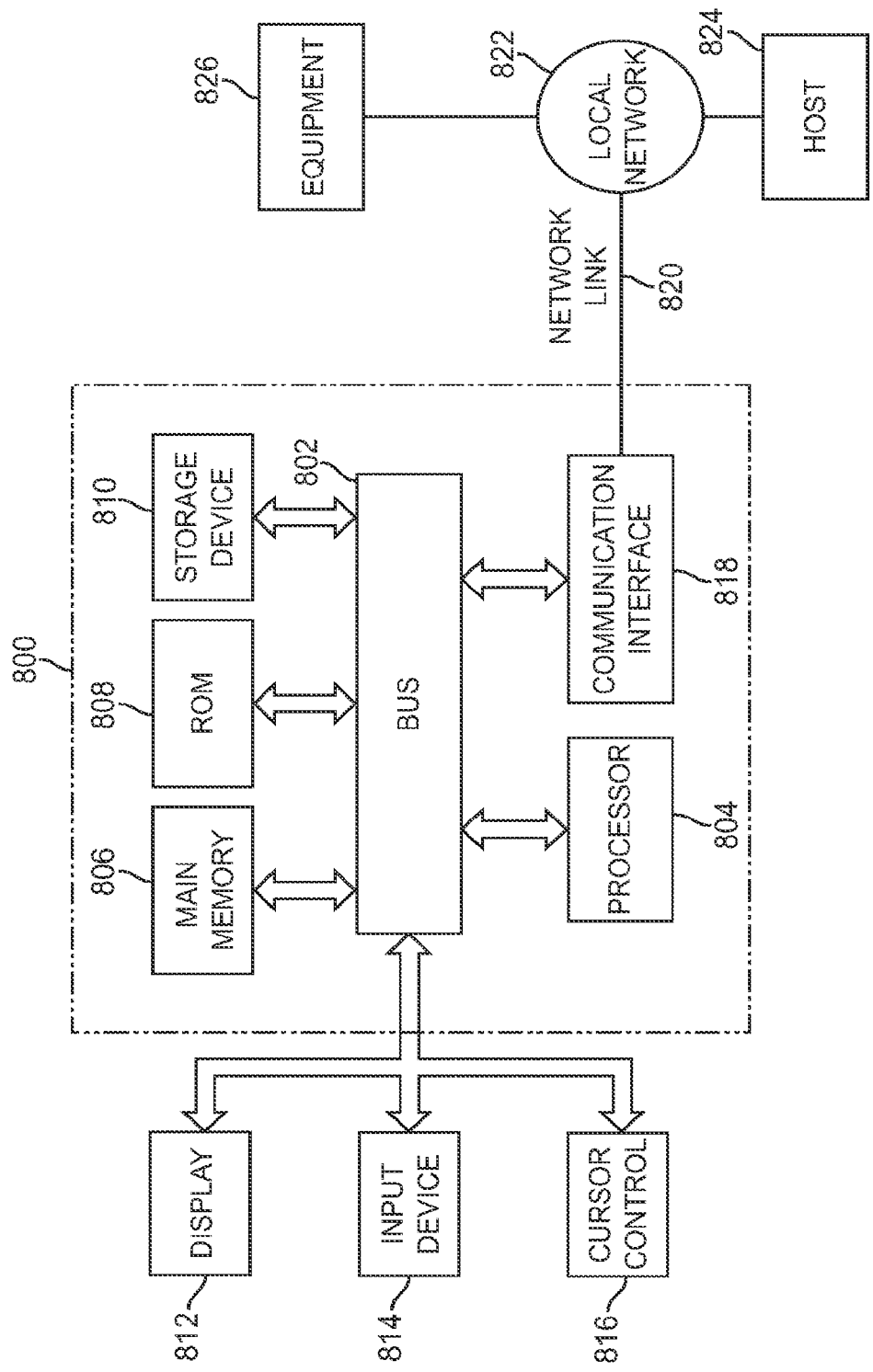
FIG. 5 is a block diagram of a computer system architecture, with which embodiments described herein may be implemented.

FIG. 5 is a block diagram that illustrates an embodiment of a computer system 800 upon which an embodiment of the invention may be implemented. Computer system 800 includes a bus 802 or other communication mechanism for communicating information, and a processor 804 coupled with the bus 802 for processing information. The processor 804 may be an example of the processor 54 of FIG. 1, or another processor that is used to perform various functions described herein. In some cases, the computer system 800 may be used to implement the processor 54. The computer system 800 also includes a main memory 806, such as a random access memory (RAM) or other dynamic storage device, coupled to the bus 802 for storing information and instructions to be executed by the processor 804. The main memory 806 also may be used for storing temporary variables or other intermediate information during execution of instructions to be executed by the processor 804. The computer system 800 further includes a read only memory (ROM) 808 or other static storage device coupled to the bus 802 for storing static information and instructions for the processor 804. A data storage device 810, such as a magnetic disk or optical disk, is provided and coupled to the bus 802 for storing information and instructions.

The computer system 800 may be coupled via the bus 802 to a display 812, such as a cathode ray tube (CRT) or a flat panel, for displaying information to a user. An input device 814, including alphanumeric and other keys, is coupled to the bus 802 for communicating information and command selections to processor 804. Another type of user input device is cursor control 816, such as a mouse, a trackball, or cursor direction keys for communicating direction information and command selections to processor 804 and for controlling cursor movement on display 812. This input device typically has two degrees of freedom in two axes, a first axis (e.g., x) and a second axis (e.g., y), that allows the device to specify positions in a plane.

The computer system 800 may be used for performing various functions (e.g., calculation) in accordance with the embodiments described herein. According to one embodiment, such use is provided by computer system 800 in response to processor 804 executing one or more sequences of one or more instructions contained in the main memory 806. Such instructions may be read into the main memory 806 from another computer-readable medium, such as storage device 810. Execution of the sequences of instructions contained in the main memory 806 causes the processor 804 to perform the process steps described herein. One or more processors in a multi-processing arrangement may also be employed to execute the sequences of instructions contained in the main memory 806. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to the processor 804 for execution. Such a medium may take many forms, including but not limited to, non-volatile media, volatile media, and transmission media. Non-volatile media includes, for example, optical or magnetic disks, such as the storage device 810. Volatile media includes dynamic memory, such as the main memory 806. Transmission media includes coaxial cables, copper wire and fiber optics, including the wires that comprise the bus 802. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to the processor 804 for execution. For example, the instructions may initially be carried on a magnetic disk of a remote computer. The remote computer can load the instructions into its dynamic memory and send the instructions over a telephone line using a modem. A modem local to the computer system 800 can receive the data on the telephone line and use an infrared transmitter to convert the data to an infrared signal. An infrared detector coupled to the bus 802 can receive the data carried in the infrared signal and place the data on the bus 802. The bus 802 carries the data to the main memory 806, from which the processor 804 retrieves and executes the instructions. The instructions received by the main memory 806 may optionally be stored on the storage device 810 either before or after execution by the processor 804.

The computer system 800 also includes a communication interface 818 coupled to the bus 802. The communication interface 818 provides a two-way data communication coupling to a network link 820 that is connected to a local network 822. For example, the communication interface 818 may be an integrated services digital network (ISDN) card or a modem to provide a data communication connection to a corresponding type of telephone line. As another example, the communication interface 818 may be a local area network (LAN) card to provide a data communication connection to a compatible LAN. Wireless links may also be implemented. In any such implementation, the communication interface 818 sends and receives electrical, electromagnetic or optical signals that carry data streams representing various types of information.

The network link 820 typically provides data communication through one or more networks to other devices. For example, the network link 820 may provide a connection through local network 822 to a host computer 824 or to equipment 826 such as a radiation beam source or a switch operatively coupled to a radiation beam source. The data streams transported over the network link 820 can comprise electrical, electromagnetic or optical signals. The signals through the various networks and the signals on the network link 820 and through the communication interface 818, which carry data to and from the computer system 800, are exemplary forms of carrier waves transporting the information. The computer system 800 can send messages and receive data, including program code, through the network(s), the network link 820, and the communication interface 818.

Although particular embodiments have been shown and described, it will be understood that they are not intended to limit the present inventions, and it will be obvious to those skilled in the art that various changes and modifications may be made without departing from the spirit and scope of the present inventions. The specification and drawings are, accordingly, to be regarded in an illustrative rather than restrictive sense. The present inventions are intended to cover alternatives, modifications, and equivalents, which may be included within the spirit and scope of the present inventions as defined by the claims.

What is claimed:

1. A method of delivering radiation in a session, comprising:
    executing at least a part of a first package of a treatment plan to deliver radiation towards a patient using a radiation system, wherein the radiation is delivered based at least in part on a physiological phase or a position of the patient;
    executing a transition of the treatment plan for changing a configuration of the radiation system when no radiation is being delivered by the radiation system;
    executing at least a part of a second package of the treatment plan to deliver additional radiation towards the patient;
    automatically stopping a delivery of radiation during execution of the first or the second package in response to a breathing of the patient not meeting a criterion, wherein the act of stopping the delivery of radiation results in non-delivered radiation for the first or the second package; and
    delivering radiation to make up at least a part of the non-delivered radiation.

2. The method of claim 1, wherein the act of stopping the delivery of radiation places the first package or the second package in a hold state for a prescribed duration.

3. The method of claim 2, further comprising determining if a breathing of the patient meets the criterion during the hold state.

4. The method of claim 3, further comprising lifting the hold state if the breathing meets the criterion, wherein the radiation is delivered to make up the at least a part of the non-delivered radiation in response to the hold state being lifted.

5. The method of claim 3, further comprising executing a third package of the treatment plan to deliver additional radiation towards the patient if the breathing does not meet the criterion by an end of the hold state, wherein the act of delivering radiation to make up the at least a part of the non-delivered radiation is performed after the third package is executed.

6. The method of claim 3, further comprising selecting the third package from a plurality of packages before the third package is executed.

7. The method of claim 6, wherein the third package is selected based on requirements of remaining packages that need to be delivered.

8. The method of claim 6, wherein the third package is selected based on the third package having a delivery requirement that is a closest to that of a current system configuration.

9. The method of claim 8, wherein the delivery requirement comprises one or both of a prescribed source position and prescribed leaves' positions.

10. The method of claim 1, further comprising providing a user interface for prescribing at least a part of the treatment plan that includes the first package and the transition, the user interface comprising a screen displaying graphics for allowing a user to input information, wherein the graphics are generated using a processing unit;
    wherein the graphics include a first package input area for allowing the user to define the first package that prescribes one or more parameters for delivering radiation; and
    wherein the graphics include a first transition input area for allowing the user to define the transition that prescribes one or more parameters for operating one or more components of the treatment system to change the configuration of the treatment system while radiation is not being delivered.

11. A radiation system for delivering radiation in a session, comprising:
    a processing unit configured to
        execute at least a part of a first package of a treatment plan to deliver radiation towards a patient based at least in part on a physiological phase or a position of the patient,
        execute a transition of the treatment plan for changing a configuration of the radiation system when no radiation is being delivered by the radiation system,
        execute at least a part of a second package of the treatment plan for delivering additional radiation towards the patient,
        automatically stop a delivery of radiation during execution of the first package or the second package in response to a breathing of the patient not meeting a criterion, wherein the act of stopping the delivery of radiation results in non-delivered radiation for the first package or the second package, and
        operate one or more components of the radiation system radiation to deliver radiation to make up at least a part of the non-delivered radiation.

12. The system of claim 11, wherein the processing unit is configured to stop the delivery of radiation to place the first package or the second package in a hold state for a prescribed duration.

13. The system of claim 12, wherein the processing unit is configured to determine if a breathing of the patient meets the criterion during the hold state.

14. The system of claim 13, wherein the processing unit is configured to lift the hold state if the breathing meets the criterion, and wherein the processing unit is configured to operate the one or more components of the radiation system to deliver the radiation to make up the at least a part of the non-delivered radiation in response to the hold state being lifted.

15. The system of claim 13, wherein the processing unit is configured to execute a third package of the treatment plan for delivering additional radiation towards the patient if the breathing does not meet the criterion by an end of the hold state, wherein the processing unit is configured to operate the one or more components of the radiation system to deliver the radiation to make up the at least a part of the non-delivered radiation after the third package is executed.

16. The system of claim 13, wherein the processing unit is configured to select the third package from a plurality of packages before the third package is executed.

17. The system of claim 16, wherein the processing unit is configured to select the third package based on requirements of remaining packages that need to be delivered.

18. The system of claim 16, wherein the processing unit is configured to select the third package based on the third package having a delivery requirement that is a closest to that of a current system configuration.

19. The system of claim 18, wherein the delivery requirement comprises one or both of a prescribed source position and prescribed leaves' positions.

20. A user interface for prescribing at least a part of a radiation treatment plan, comprising:
a screen displaying graphics for allowing a user to input information, wherein the graphics are generated using a processing unit;
wherein the graphics include a first package input area for allowing the user to define a first package that prescribes one or more parameters for delivering radiation; and
wherein the graphics include a first transition input area for allowing the user to define a first transition that prescribes one or more parameters for operating one or more components of a treatment machine while radiation is not being delivered.

21. The user interface of claim 20, wherein the one or more parameters for delivering radiation comprises one or more of a prescribed gantry starting position, a prescribed gantry ending position, a first collimator profile, a second collimator profile, a leaf sequence, a gantry tilt angle, a radiation source tilt angle, a patient support position, a gantry speed, a target fluence, a dose rate, a beam energy, and a beam-on condition.

22. The user interface of claim 20, wherein the first package prescribes a gantry to be moved from a first gantry position to a second gantry position for radiation delivery.

23. The user interface of claim 20, wherein the first package prescribes a collimator be configured from a first collimator profile to a second collimator profile for radiation delivery.

24. The user interface of claim 20, wherein the one or more parameters for operating the one or more components of the treatment machine comprise one or more of a prescribed gantry starting position, a prescribed gantry ending position, a first collimator profile, a second collimator profile, and a patient support position.

25. The user interface of claim 20, wherein the first transition prescribes a gantry to be moved from a first gantry position to a second gantry position while radiation is not being delivered.

26. The user interface of claim 20, wherein the first transition prescribes a collimator be configured from a first collimator profile to a second collimator profile while radiation is not being delivered.

27. The user interface of claim 20, wherein the graphics include a second package input area for allowing the user to define a second package.

28. The user interface of claim 20, wherein the graphics include a second transition input area for allowing the user to define a second transition.

* * * * *